US008633302B2

(12) United States Patent
Hepbildikler et al.

(10) Patent No.: US 8,633,302 B2
(45) Date of Patent: Jan. 21, 2014

(54) VARIABLE TANGENTIAL FLOW FILTRATION

(75) Inventors: Stefan Hepbildikler, Munich (DE); Wolfgang Kuhne, Penzberg (DE); Eva Rosenberg, Munich (DE); Gerhard Winter, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 745 days.

(21) Appl. No.: 12/668,661

(22) PCT Filed: Jul. 15, 2008

(86) PCT No.: PCT/EP2008/005766
§ 371 (c)(1),
(2), (4) Date: Jan. 12, 2010

(87) PCT Pub. No.: WO2009/010269
PCT Pub. Date: Jan. 22, 2009

(65) Prior Publication Data
US 2010/0196961 A1 Aug. 5, 2010

(30) Foreign Application Priority Data
Jul. 17, 2007 (EP) .................................... 07013948

(51) Int. Cl.
*A23J 1/00* (2006.01)
*C07K 1/00* (2006.01)
*C07K 14/00* (2006.01)
*C07K 16/00* (2006.01)

(52) U.S. Cl.
USPC .......................................... 530/412; 530/414

(58) Field of Classification Search
None
See application file for complete search history.

(56) References Cited

U.S. PATENT DOCUMENTS

| 5,490,937 | A | 2/1996 | Van Reis |
| 6,252,055 | B1 | 6/2001 | Relton |
| 2004/0167320 | A1 | 8/2004 | Couto et al. |
| 2006/0051347 | A1 | 3/2006 | Winter |
| 2006/0182740 | A1 | 8/2006 | Yang et al. |

FOREIGN PATENT DOCUMENTS

| EP | 0907378 | 4/1999 |
| WO | 97/45140 | 4/1997 |
| WO | 97/45140 | 12/1997 |
| WO | 2004/076695 | 9/2004 |
| WO | 2005091801 | 6/2005 |
| WO | 2006/031560 | 3/2006 |
| WO | 2006/091801 A2 | 8/2006 |

OTHER PUBLICATIONS (Translation of Jap Off Act in Corres Jap Appl 2010516413 Jul. 24, 2012).
Van Reis et al: "Bioprocess membrane technology" Jour. of Membrane Science 297:1-2 (2007) 16-50 XP02208062.
Reis Van R et al: "Membrane separations in biotechnology" Current Opinion in Biotechnology 12:2 (2001) 208-211 XP002317550.
Low et al: "Future of antibody purification" Journal of Chromatography B: Biomedical Sciences & Applications, 848:1 (2007) 48-63 XP005922827.
Dosmar, M. et al, "Factors influencing Ultrafiltration Scale-Up" Bioprocess International, Informa Life Sciences Group,3:40-50 (2005) XP009090780.
Van Reis R et al, "High-performance tangential flow filtration using charged membranes" Journal of Membrane Science 159:1-2 (1999) 133-142 XP004169169.
Velez D et al: "Use of tangential flow filtration in perfusion propagation of hybridoma cells for production of monoclonal antibodies" Biotechnology and Bioengineering 33;7 (1989) 938-940 XP000005263.
Membrane Technology, "TFF cassettes offer high reliability and performance" 2006:11 (2006) p. 4, XP005772756.
Gerhart et al, Fundamentals of Fluid Mechanics (1992) 2nd Ed.
Ahrer, et al, Jour of Membrane Sci 274 (2006) 108-115.
Cheryan, M. Ultrafiltration and Microfiltration Handbook (1998).
Lou et al, "High Concentration UF/DF of a Monoclonal Antibody" Bioproces Technical vol. 4 (2006) 44-47.
Shire, S et al, Jour. of Pharmaceutical Sciences93:6 (2004) 1390-1402.
Uber, D C et al, Biotechniques 11:5 (1991) 642-647.
Millipore Technical Brief: Protein Concentration and Diafiltration by Tangential Flow Filtration, 2003.
The Communication of the notice of opposition by the European Patent Office, issued on Oct. 2, 2013, in the co-pending European Patent No. EP 2170949., pp. 29.
Rosenberg et al., "Ultrafiltration concentration of monoclonal antibody solutions: Development of an optimized method minimizing aggregation" Journal of Membrane Science 342(1-2):50-59.

*Primary Examiner* — Daniel E Kolker
*Assistant Examiner* — James Rogers

(57) ABSTRACT

The current invention reports a method for concentrating an immunoglobulin solution by tangential flow filtration wherein the transmembrane pressure and the cross-flow are variable.

13 Claims, 15 Drawing Sheets

VARIABLE TANGENTIAL FLOW FILTRATION

The current invention is in the field of protein concentration, to be more precise it relates to the use of tangential flow filtration (TFF) for immunoglobulin concentration.

BACKGROUND OF THE INVENTION

Proteins and especially immunoglobulins play an important role in today's medical portfolio. Expression systems for the production of recombinant polypeptides are well-known in the state of the art and are described by, e.g., Marino, M. H., Biopharm. 2 (1989) 18-33; Goeddel, D. V., et al., Methods Enzymol. 185 (1990) 3-7; Wurm, F., and Bernard, A., Curr. Opin. Biotechnol. 10 (1999) 156-159. Polypeptides for use in pharmaceutical applications are mainly produced in mammalian cells such as CHO cells, NSO cells, Sp2/0 cells, COS cells, HEK cells, BHK cells, PER.C6® cells, and the like.

For human application every pharmaceutical substance has to meet distinct criteria. To ensure the safety of biopharmaceutical agents to humans, for example, nucleic acids, viruses, and host cell proteins, which would cause severe harm, have to be removed. To meet the regulatory specification one or more purification steps have to follow the manufacturing process. Among other, purity, throughput, and yield play an important role in determining an appropriate purification process.

Due to their chemical and physical properties, such as molecular weight and domain architecture including secondary modifications, the downstream processing of immunoglobulins is very complicated. For example, are not only for formulated drugs but also for intermediates in downstream processing (DSP) concentrated solutions required to achieve low volumes for economic handling and application storage. Furthermore short concentration times are favored to ensure smooth processes and short operating times. In this context imperfect TFF processes especially after final purification steps can cause sustained damage even affecting drug product. The correlation between shear stress and aggregation in tangential flow concentration processes for monoclonal antibody (mAb) intermediate solutions was investigated by Ahrer, K., et al. (J. Membr. Sci. 274 (2006) 108-115). The influence of concentration time and selected flow and pressure on process performance and aggregation status was monitored (see e.g. Dosmar, M., et al., Bioprocess Int. 3 (2005) 40-50; Luo, R., et al., Bioprocess Int. 4 (2006) 44-46).

Mahler, H.-C., et al. (Eur. J. Pharmaceut. Biopharmaceut. 59 (2005) 407-417) reported the induction and analysis of aggregates in a liquid IgG1-antibody formulation formed by different agitation stress methods. In U.S. Pat. No. 6,252,055 a concentrated monoclonal antibody preparation is reported. A method for producing a concentrated antibody preparation is reported in US 2006/0182740. A combined process including an ultrafiltration, a diafiltration, and a second ultrafiltration sequence is reported in US 2006/0051347. In EP 0 907 378 is reported a process for concentrating an antibody preparation using a cross-flow ultrafiltration with a fixed recirculation rate of 250 ml/min. Methods for tangential flow filtration and an apparatus therefore is reported in US 2004/0167320. In WO 97/45140 a concentrated antibody solution is reported.

SUMMARY OF THE INVENTION

The current invention provides a method for the concentration of solutions containing recombinantly produced immunoglobulins.

In more detail, one aspect of the current invention is a method for concentrating an immunoglobulin solution by tangential flow filtration wherein the transmembrane pressure and the cross-flow, which are applied, are variable with
a) a transmembrane pressure of from 1.4 bar to 1.6 bar and a cross-flow of from 75 ml/min. to 90 ml/min. in a concentration range up to 30 mg immunoglobulin per ml of solution to be concentrated,
b) a transmembrane pressure of from 0.8 bar to 0.9 bar and a cross-flow of from 140 ml/min. to 160 ml/min. in a concentration range of from 15 mg/ml up to 55 mg/ml, and
c) a transmembrane pressure of from 0.8 bar to 0.9 bar and a cross-flow of from 120 ml/min. to 140 ml/min. in a concentration range of more than 45 mg/ml.

In one embodiment the concentration range in step c) is of from 50 mg/ml up to 275 mg/ml. In a preferred embodiment the concentration range in step c) is of from 50 mg/ml up to 180 mg/ml. In a more preferred embodiment the concentration range in step c) is of from 50 mg/ml up to 130 mg/ml. In another embodiment the transmembrane pressure and cross-flow are 1.5 bar and 80 ml/min. in step a), 0.85 bar and 150 ml/min. in step b), and/or 0.85 bar and 130 ml/min. in step c). In another embodiment the immunoglobulin solution is a buffered, aqueous immunoglobulin solution.

Another aspect of the current invention is a method for producing a heterologous immunoglobulin comprising the following steps in this order:
a) providing a recombinant mammalian cell comprising one or more nucleic acids encoding a heterologous immunoglobulin,
b) cultivating the cell of step a) under conditions suitable for the expression of the heterologous immunoglobulin,
c) recovering the heterologous immunoglobulin from the recombinant mammalian cell or the culture medium,
d) concentrating the obtained aqueous, buffered solution comprising the heterologous immunoglobulin using a tangential flow filtration with variable transmembrane pressure and cross flow.

In one embodiment step d) of the method comprises concentrating the obtained aqueous, buffered solution using a tangential flow filtration with variable transmembrane pressure and cross flow with
i) a transmembrane pressure of from 1.4 bar to 1.6 bar and a cross-flow of from 75 ml/min. to 90 ml/min. in a concentration range up to 30 mg immunoglobulin per ml of solution to be concentrated,
ii) a transmembrane pressure of from 0.8 bar to 0.9 bar and a cross-flow of from 140 ml/min. to 160 ml/min. in a concentration range of from 15 mg/ml up to 55 mg/ml, and
iii) a transmembrane pressure of from 0.8 bar to 0.9 bar and a cross-flow of from 120 ml/min. to 140 ml/min. in a concentration range of more than 45 mg/ml.

In another embodiment the method comprises prior to step d) or after step d) the following step:
e) purifying the aqueous, buffered solution containing the heterologous immunoglobulin.

In another embodiment the heterologous immunoglobulin is a complete immunoglobulin, or an immunoglobulin fragment, or an immunoglobulin conjugate. In one embodiment the mammalian cell is a CHO cell, a BHK cell, a NSO cell, a Sp2/0 cell, a COS cell, a HEK cell, or a PER.C6® cell.

DETAILED DESCRIPTION OF THE INVENTION

The current invention reports a method for concentrating immunoglobulin solutions to a concentration of more than 100 mg/ml. It has been surprisingly found that with a method according to the invention this can be achieved with low aggregate formation and in short time.

The terms "tangential flow filtration" or "TFF", which are used interchangeably within the current invention, denote a filtration process wherein a solution containing a polypeptide to be concentrated flows along, i.e. tangential, to the surface of a filtration membrane. The filtration membrane has a pore size with a certain cut off value. In one embodiment the cut off value is in the range of 20 kDa to 50 kDa, preferably of 30 kDa. This filtration process is a kind of an ultrafiltration process. The term "cross-flow" denotes the flow of the solution to be concentrated tangential to the membrane (retentate flow). The term "flux" or "permeate flow", which can be used interchangeably within the current invention, denotes the flow of fluid across the membrane, i.e. through the pores of the membrane. That is, it denotes the volumetric rate of flow of the permeate through the membrane. A flow is usually given in terms of volume per unit membrane area per unit time as liters/m$^2$/h (LMH). In one embodiment the cross-flow is characterized in that the cross-flow is in ml/min for a membrane area of 0.02 m$^2$. In another embodiment the cross flow is in the individual steps 240 l/m$^2$/h, 450 l/m$^2$/h, and 390 l/m$^2$/h. The permeate comprises the solvent of the solution to be concentrated as well as molecules with a molecular weight below the cut off value of the employed membrane but not the heterologous immunoglobulin. The terms "transmembrane pressure" or "TMP", which can be used interchangeably within the current invention, denote the pressure which is applied to drive the solvent and components smaller than the cut off value of the filtration membrane through the pores of the filtration membrane. The transmembrane pressure is an average pressure of the inlet, outlet and permeate and can be calculated as:

$$TMP = \frac{(p_{in} + p_{out})}{2} - p_{permeate}$$

The term "immunoglobulin" refers to a protein consisting of one or more polypeptide(s) substantially encoded by immunoglobulin genes. The recognized immunoglobulin genes include the different constant region genes as well as the myriad immunoglobulin variable region genes. Immunoglobulins may exist in a variety of formats, including, for example, Fv, Fab, and F(ab)$_2$ as well as single chains (scFv) or diabodies (e.g. Huston, J. S., et al., Proc. Natl. Acad. Sci. USA 85 (1988) 5879-5883; Bird, R. E., et al., Science 242 (1988) 423-426; in general, Hood et al., Immunology, Benjamin N.Y., 2nd edition (1984); and Hunkapiller, T. and Hood, L., Nature 323 (1986) 15-16).

The term "complete immunoglobulin" denotes an immunoglobulin which comprises two so called light immunoglobulin chain polypeptides (light chain) and two so called heavy immunoglobulin chain polypeptides (heavy chain). Each of the heavy and light immunoglobulin chain polypeptides of a complete immunoglobulin contains a variable domain (variable region) (generally the amino terminal portion of the polypeptide chain) comprising binding regions that are able to interact with an antigen. Each of the heavy and light immunoglobulin chain polypeptides of a complete immunoglobulin also comprises a constant region (generally the carboxyl terminal portion). The constant region of the heavy chain mediates the binding of the antibody i) to cells bearing a Fc gamma receptor (FcγR), such as phagocytic cells, or ii) to cells bearing the neonatal Fc receptor (FcRn) also known as Brambell receptor. It also mediates the binding to some factors including factors of the classical complement system such as component (C1q). The variable domain of an immunoglobulin's light or heavy chain in turn comprises different segments, i.e. four framework regions (FR) and three hypervariable regions (CDR).

The term "immunoglobulin fragment" denotes a polypeptide comprising at least one domain of the variable domain, the $C_H1$ domain, the hinge-region, the $C_H2$ domain, the $C_H3$ domain, the $C_H4$ domain of a heavy chain, the variable domain or the $C_L$ domain of a light chain. Also comprised are derivatives and variants thereof. For example, a variable domain, in which one or more amino acids or amino acid regions are deleted, may be present.

The term "immunoglobulin conjugate" denotes a polypeptide comprising at least one domain of an immunoglobulin heavy or light chain conjugated via a peptide bond to a further polypeptide. The further polypeptide is a non-immunoglobulin peptide, such as a hormone, or growth receptor, or antifusogenic peptide, or complement factor, or the like.

General chromatographic methods and their use are known to a person skilled in the art. See for example, Chromatography, 5$^{th}$ edition, Part A: Fundamentals and Techniques, Heftmann, E. (ed.), Elsevier Science Publishing Company, New York, (1992); Advanced Chromatographic and Electromigration Methods in Biosciences, Deyl, Z. (ed.), Elsevier Science BV, Amsterdam, The Netherlands, (1998); Chromatography Today, Poole, C. F., and Poole, S. K., Elsevier Science Publishing Company, New York, (1991); Scopes, Protein Purification: Principles and Practice (1982); Sambrook, J., et al. (ed.), Molecular Cloning: A Laboratory Manual, second edition, Cold Spring Harbor Laboratory Press, Cold Spring Harbor, N.Y., 1989; or Current Protocols in Molecular Biology, Ausubel, F. M., et al. (eds), John Wiley & Sons, Inc., New York.

For the purification of recombinantly produced heterologous immunoglobulins often a combination of different column chromatography steps is employed. Generally a protein A affinity chromatography is followed by one or two additional separation steps. The final purification step is a so called "polishing step" for the removal of trace impurities and contaminants like aggregated immunoglobulins, residual HCP (host cell protein), DNA (host cell nucleic acid), viruses, or endotoxins. For this polishing step often an anion exchange material in a flow-through mode is used.

Different methods are well established and widespread used for protein recovery and purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, azaarenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

The term "heterologous immunoglobulin" denotes an immunoglobulin which is not naturally produced by a mammalian cell. The immunoglobulin produced according to the method of the invention is produced by recombinant means. Such methods are widely known in the state of the art and comprise protein expression in eukaryotic cells with subsequent recovery and isolation of the heterologous immunoglobulin, and usually purification to a pharmaceutically acceptable purity. For the production, i.e. expression, of an immunoglobulin a nucleic acid encoding the light chain and a nucleic acid encoding the heavy chain are inserted each into an expression cassette by standard methods. Nucleic acids encoding immunoglobulin light and heavy chains are readily isolated and sequenced using conventional procedures. Hybridoma cells can serve as a source of such nucleic acids. The expression cassettes may be inserted into an expression plasmid(s), which is (are) then transfected into the host cell, which does not otherwise produce immunoglobulins. Expression is performed in appropriate prokaryotic or eukaryotic host cells and the immunoglobulin is recovered from the cells after lysis or from the culture supernatant.

The term "immunoglobulin solution" as used within the current application denotes an aqueous, buffered solution containing a complete immunoglobulin, an immunoglobulin fragment, or an immunoglobulin conjugate. This solution may be, e.g., a culture supernatant, or a column chromatography eluate, or a polished immunoglobulin solution.

"Heterologous DNA" or "heterologous polypeptide" refers to a DNA molecule or a polypeptide, or a population of DNA molecules or a population of polypeptides, that do not exist naturally within a given host cell. DNA molecules heterologous to a particular host cell may contain DNA derived from the host cell species (i.e. endogenous DNA) so long as that host DNA is combined with non-host DNA (i.e. exogenous DNA). For example, a DNA molecule containing a non-host DNA segment encoding a polypeptide operably linked to a host DNA segment comprising a promoter is considered to be a heterologous DNA molecule. Conversely, a heterologous DNA molecule can comprise an endogenous structural gene operably linked with an exogenous promoter. A peptide or polypeptide encoded by a non-host DNA molecule is a "heterologous" peptide or polypeptide.

The term "under conditions suitable for the expression of the heterologous immunoglobulin" denotes conditions which are used for the cultivation of a mammalian cell expressing an immunoglobulin and which are known to or can easily be determined by a person skilled in the art. It is also known to a person skilled in the art that these conditions may vary depending on the type of mammalian cell cultivated and type of immunoglobulin expressed. In general the mammalian cell is cultivated at a temperature of from 20° C. to 40° C., and for a period of time sufficient to allow effective protein production of the immunoglobulin, e.g. of from 4 to 28 days.

The term "recombinant mammalian cell" refers to a cell into which a nucleic acid, e.g. encoding a heterologous polypeptide, can be or is introduced/transfected. The term "cell" includes cells which are used for the expression of nucleic acids. In one embodiment the mammalian cell is a CHO cell (e.g. CHO K1, CHO DG44), or a BHK cell, or a NSO cell, or a SP2/0 cell, or a HEK 293 cell, or a HEK 293 EBNA cell, or a PER.C6® cell, or a COS cells. In a preferred embodiment the mammalian cell is a CHO cell, or a BHK cell, or HEK cell, or Sp2/0 cell, or a PER.C6® cell. As used herein, the expression "cell" includes the subject cell and its progeny. Thus, the term "recombinant cell" include the primary transfected cell and cultures including the progeny cells derived there from without regard to the number of transfers. It is also understood that all progeny may not be precisely identical in DNA content, due to deliberate or inadvertent mutations. Variant progeny that have the same function or biological activity as the originally transformed cell are included.

The term "buffered" as used within this application denotes a solution in which changes of pH due to the addition or release of acidic or basic substances is leveled by a buffer substance. Any buffer substance resulting in such an effect can be used. In one embodiment pharmaceutically acceptable buffer substances are used, such as e.g. phosphoric acid or salts thereof, acetic acid or salts thereof, citric acid or salts thereof, morpholine or salts thereof, 2-(N-morpholino) ethanesulfonic acid or salts thereof, Histidine or salts thereof, Glycine or salts thereof, or tris (hydroxymethyl) aminomethane (TRIS) or salts thereof. In a preferred embodiment the buffer substance is phosphoric acid or salts thereof, acetic acid or salts thereof, or citric acid or salts thereof, or histidine or salts thereof. Optionally the buffered solution may comprise an additional salt, such as e.g. sodium chloride, and/or sodium sulphate, and/or potassium chloride, and/or potassium sulfate, and/or sodium citrate, and/or potassium citrate. In one embodiment of the invention the pH value of the buffered aqueous solution is of from pH 3.0 to pH 10.0, preferably of from pH 3.0 to pH 7.0, more preferred of from pH 4.0 to pH 6.0, and most preferred of from pH 4.5 to pH 5.5.

It has now surprisingly been found that with a tangential flow filtration (TFF) method according to the current invention in which the transmembrane pressure and cross-flow are variable during the filtration process and are adapted depending on the actual concentration of the immunoglobulin in the solution to be concentrated a concentrated immunoglobulin solution with low aggregate formation can be obtained in a short time. That is, it has surprisingly been found that aggregate formation during tangential flow filtration is low if a TFF method according to the invention is applied, i.e. a method in which during the filtration process the transmembrane pressure is changed and adapted according to the actual concentration of the antibody solution. The method according to the invention is a variable method compared to constant methods as known from the art, i.e. to methods in which the transmembrane pressure is adopted prior to the filtration process and is held constant during the entire tangential flow filtration process.

The current invention comprises a method for concentrating an immunoglobulin solution by tangential flow filtration wherein the transmembrane pressure and the cross-flow, which are applied, are variable and changed during the filtration process depending on the immunoglobulin concentration in the concentrated immunoglobulin solution, whereby
  a) a transmembrane pressure of from 1.4 bar to 1.6 bar and a cross-flow of from 75 ml/min. to 90 ml/min. is applied in a concentration range up to 30 mg immunoglobulin per ml of the solution to be concentrated,
  b) a transmembrane pressure of from 0.8 bar to 0.9 bar and a cross-flow of from 140 ml/min. to 160 ml/min. is applied in a concentration range of from 15 mg/ml up to 55 mg/ml, and
  c) a transmembrane pressure of from 0.8 bar to 0.9 bar and a cross-flow of from 120 ml/min. to 140 ml/min. is applied in a concentration range of more than 45 mg/ml.

A correlation between shear stress in TFF and aggregate formation exists. To evaluate the effect the flow-induced shear stress $\tau_w$ on the surface of the used membrane was calculated with the following formula $$\tau_w = \frac{d_H(\Delta p)}{4L} \text{ wherein } d_H \text{ is } d_H = 4\frac{ab}{2(a+b)}$$

based on Gerhart, et al. (Fundamentals of Fluid Mechanics, Addison-Wesley Publishing Company (1993)) and on Cheryan, et al. (Ultrafiltration and Microfiltration Handbook, second edition CRC Press LLC (1998)). In this formula $d_H$ is the hydraulic diameter, a the width, b the height, and L the length of the flow channel. Further, $\Delta p = p_i - p_o$, with $p_i$ is the applied inlet pressure, and $p_o$ is the outlet pressure. In one example a Hydrosart™ membrane (Sartocon Slice 200 Hydrosart™ of Sartorius AG, Göttingen, Germany) consisting of regenerated cellulose, with a nominal molecular weight cut off of 30 kDa and a membrane area of 0.02 m² was employed. For the used membrane cassette a hydraulic diameter of 1.08 mm was calculated. The membrane was at first operated with a standard TFF method, i.e. without a change of transmembrane pressure and cross-flow during the concentration process. Three different constant methods with preset, constant $\Delta p$ and a preset, constant transmembrane pressure (TMP) of 0.6 bar were analyzed.

TABLE 1

Overview of applied pressure differences and the corresponding shear stress.

| $\Delta p$ [bar] | $\tau_w$ [Pa] |
|---|---|
| 1.2 | 216 |
| 1.8 | 324 |
| 3.0 | 541 |

By observing flux versus ascending protein concentration there is no significant difference in the curves for processes at different $\Delta p$. But for the 3 bar mode a lower end concentration due to a high inlet pressure was observed. Compared to a concentration mode performed under a lower constant cross-flow (CF; 90 ml/min.) and a lower mean $\Delta p$ (about 0.9 bar) a higher $\Delta p$ of 1.2-1.8 bar contributes to an improved flux performance over time and a higher end concentration (TMP always 0.6 bar).

Comparing turbidity, light obscuration (LO), and dynamic light scattering (DLS) data before and after the concentration process showed that enhanced aggregate formation was found with increased shear stress (FIG. 2).

A TFF method has been developed with comparable overall process time compared to the stressing high inlet pressure mode ($\Delta p$=3 bar), based on TMP/CF-scouting experiments (see e.g. Luo, R., et al., Bioprocess Int. 4 (2006) 44-54). The method according to the invention has been developed to improve flux performance over time with reduced immunoglobulin aggregate formation, i.e. to combine a low aggregate formation and a short overall concentration time. During the developing of the method according to the invention a TMP and CF scouting was performed depending on the prevailing immunoglobulin concentration in the immunoglobulin solution to be concentrated. An method with adapted TMP and CF depending on the best flux profile at a given concentration was found. Without the disadvantage of high inlet pressure at the final stage of the concentration (see e.g. Dosmar, M., et al., Bioprocess Int. 3 (2005) 40-50) the method according to the invention showed a low aggregation burden in turbidity, LO, and DLS data for produced concentrates (see FIGS. 3 and 4). In addition a higher end concentration was achieved with the method according to the invention.

In the method according to the invention the transmembrane pressure and cross-flow are varied with respect to the actual concentration of the concentrated immunoglobulin solution. In one embodiment the method according to the invention is a variable tangential flow filtration method wherein the actual concentration of the immunoglobulin in the solution to be concentrated determines the applied transmembrane pressure and cross-flow. Thus, the transmembrane pressure and cross-flow are adjusted depending on the actual concentration of the immunoglobulin in order to reduce the stress applied and, thus, to reduce the formation of aggregated immunoglobulin molecules and to provide a short overall concentration time.

In the method according to the invention three concentration ranges are defined. The first actual concentration range of the solution to be concentrated is from 0 mg/ml to 30 mg/ml, the second actual concentration range is from 15 mg/ml to 55 mg/ml, and the third actual concentration range is from 45 mg/ml to 180 mg/ml. As it can be seen these concentration ranges are overlapping ranges. It has been found that in the overlapping concentration ranges of from 15 mg/ml to 30 mg/ml and of from 45 mg/ml to 55 mg/ml different values for the transmembrane pressure and the cross-flow can be used in the method according to the invention. In these overlapping concentration ranges any of the two TMP and CF settings can be applied without a notable effect on aggregated formation or process time.

Thus, in one embodiment of the method according to the invention the conditions from a) to b) and from b) to c) can be changed at any concentration value in the overlapping concentration ranges.

In one embodiment the concentration range in step c) is of from 50 mg/ml up to 275 mg/ml. In another embodiment the transmembrane pressure and cross-flow is 1.5 bar and 80 ml/min. in step a), 0.85 bar and 150 ml/min. in step b), and/or 0.85 bar and 130 ml/min. in step c). In another embodiment is the immunoglobulin solution a buffered, aqueous immunoglobulin solution. In one embodiment the concentration range is in step a) of 5 to 25 mg/ml, in step b) of from 25 to 50 mg/ml, and in step c) of from 50 to 140 mg/ml.

Another aspect of the current invention is a method for producing a heterologous immunoglobulin comprising the following steps in the following order:
 a) providing a recombinant mammalian cell comprising one or more nucleic acids encoding a heterologous immunoglobulin,
 b) cultivating the mammalian cell under conditions suitable for the expression of the heterologous immunoglobulin,
 c) recovering the heterologous immunoglobulin from the recombinant mammalian cell or the culture medium as aqueous, buffered solution,
 d) concentrating the obtained aqueous, buffered solution comprising the heterologous immunoglobulin using a tangential flow filtration with variable, immunoglobulin concentration dependent transmembrane pressure and cross-flow.

In one embodiment of the production method according to the invention comprises step d) concentrating the obtained aqueous, buffered solution using a tangential flow filtration with variable, immunoglobulin concentration dependent transmembrane pressure and cross-flow with
 i) a transmembrane pressure of from 1.4 bar to 1.6 bar and a cross-flow of from 75 ml/min. to 90 ml/min. in a concentration range up to 30 mg immunoglobulin per ml of solution to be concentrated,
 ii) a transmembrane pressure of from 0.8 bar to 0.9 bar and a cross-flow of from 140 ml/min. to 160 ml/min. in a concentration range of from 15 mg/ml up to 55 mg/ml, and
 iii) a transmembrane pressure of from 0.8 bar to 0.9 bar and a cross-flow of from 120 ml/min. to 140 ml/min. in a concentration range of more than 45 mg/ml.

In another embodiment the method comprises prior to, i.e. before, or after step d) the following step:

e) purifying the aqueous, buffered solution containing the heterologous immunoglobulin.

The purification in step e) can be by different methods and techniques, such as a chromatography step, or a combination of different or similar chromatographic steps, or precipitation, or salting out, or ultrafiltration, or diafiltration, or lyophilization, or buffer change, or combinations thereof, or the like.

In another embodiment the heterologous immunoglobulin is a complete immunoglobulin, or an immunoglobulin fragment, or an immunoglobulin conjugate. In one embodiment the mammalian cell is a CHO cell, a BHK cell, a NSO cell, a Sp2/0 cell, a COS cell, a HEK cell, or a PER.C6® cell. In a preferred embodiment the mammalian cell is a CHO cell, or a BHK cell, or a HEK cell, or a Sp2/0 cell, or a PER.C6® cell.

The following examples and figures are provided to aid the understanding of the present invention, the true scope of which is set forth in the appended claims. It is understood that modifications can be made in the procedures set forth without departing from the spirit of the invention.

An anti-IL-IR antibody (see e.g. WO 2005/023872) and an anti-P-selectin antibody (see e.g. WO 2005/100402) were available in sufficient quantities in our laboratories at the time of the invention and therefore the current invention is exemplified with these two immunoglobulins. Likewise the invention is in general practicable with any immunoglobulin. This exemplified description is done only by way of example and not by way of limitation of the invention.

EXAMPLE 1

Figure 1:
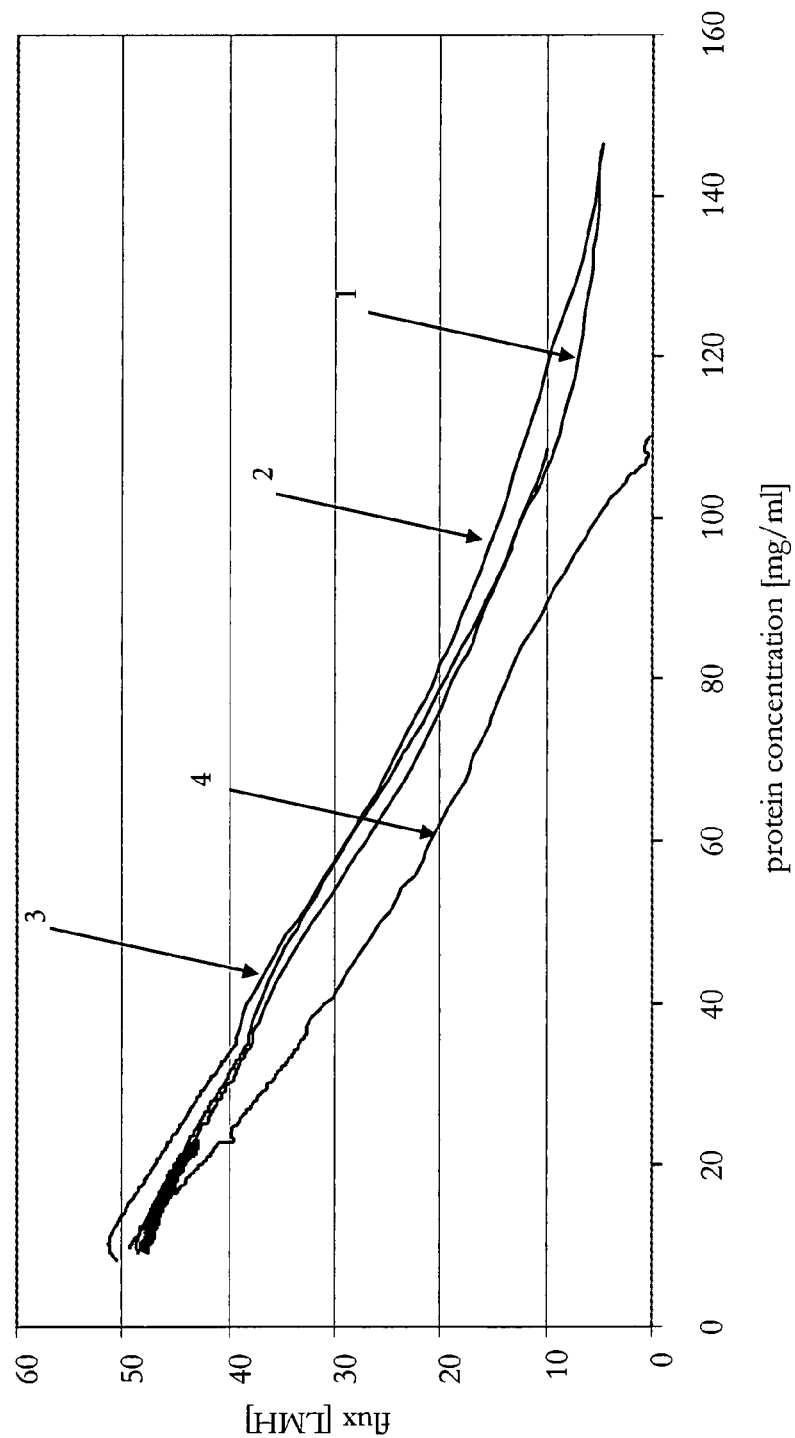
FIG. 1 Flux versus protein concentration of an anti-IL-IR antibody solution before flushing of the membrane for different constant $\Delta p$ modes and a concentration method under constant CF of 90 ml/min. 1: constant method $\Delta p=1.2$ bar, 2: constant method $\Delta p=1.8$ bar, 3: constant method $\Delta p=3.0$ bar, 4: constant method CF 90 ml/min.
Figure 2:
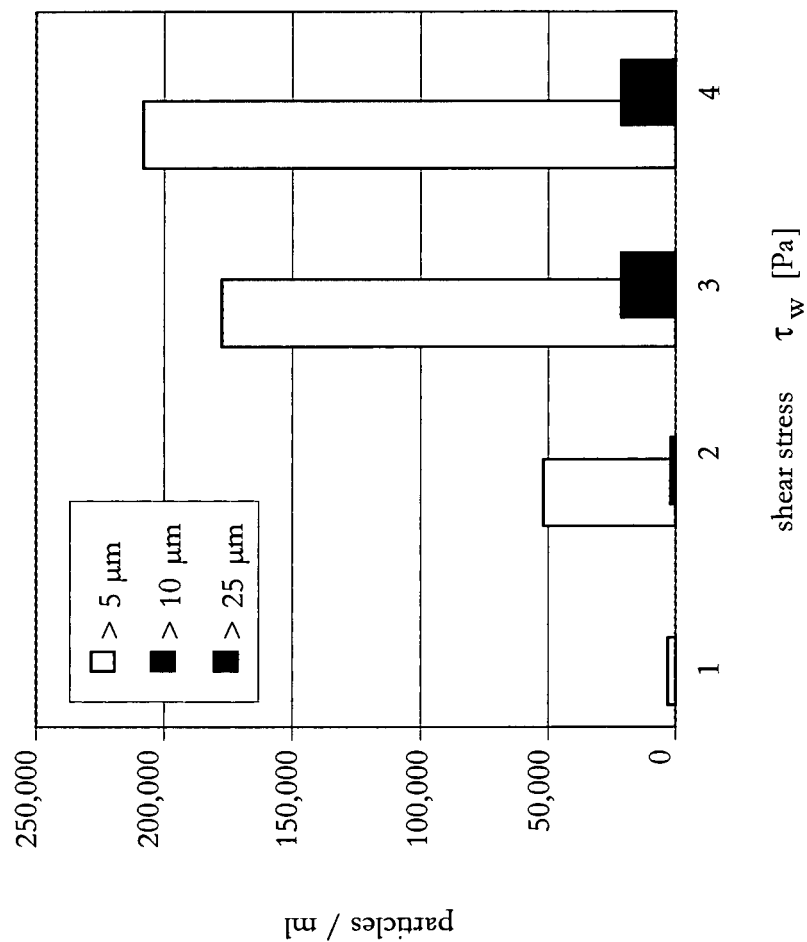
FIG. 2 Number of particles before and after concentration of an anti-IL-IR antibody solution with constant method. 1: before concentration, 2: $\tau_w=216$, 3: $\tau_w=324$, 4: $\tau_w=541$.
Figure 3:
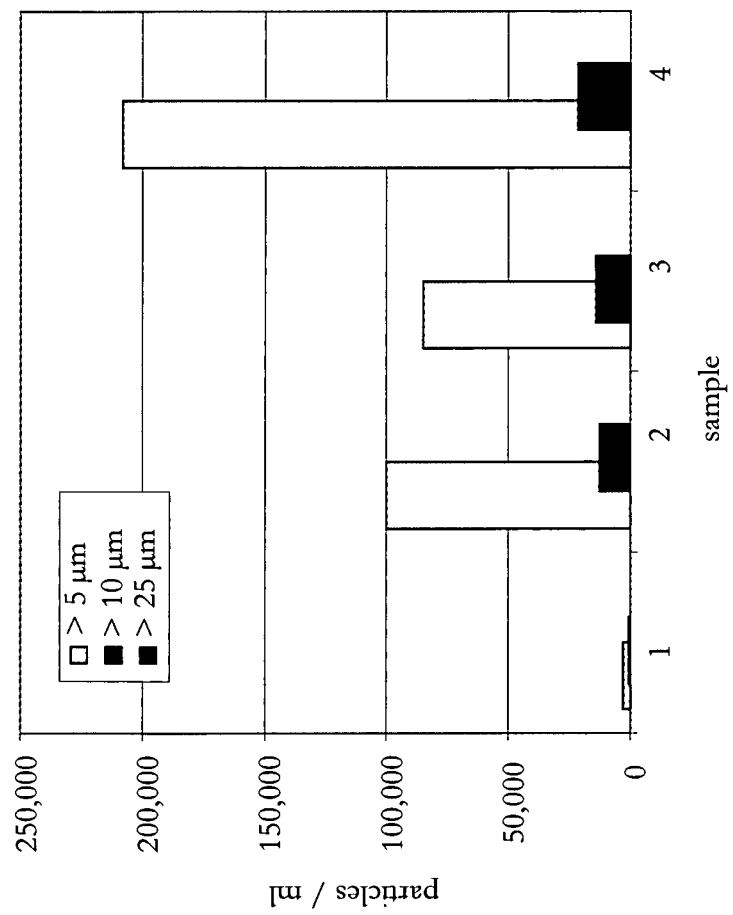
FIG. 3 Comparison of number of particles of an anti-IL-IR antibody solution before and after concentration with different methods. 1: before concentration, 2: variable method according to the invention, 3: constant method CF 90 ml/min., 4: $\tau_w=541$.
Figure 4:
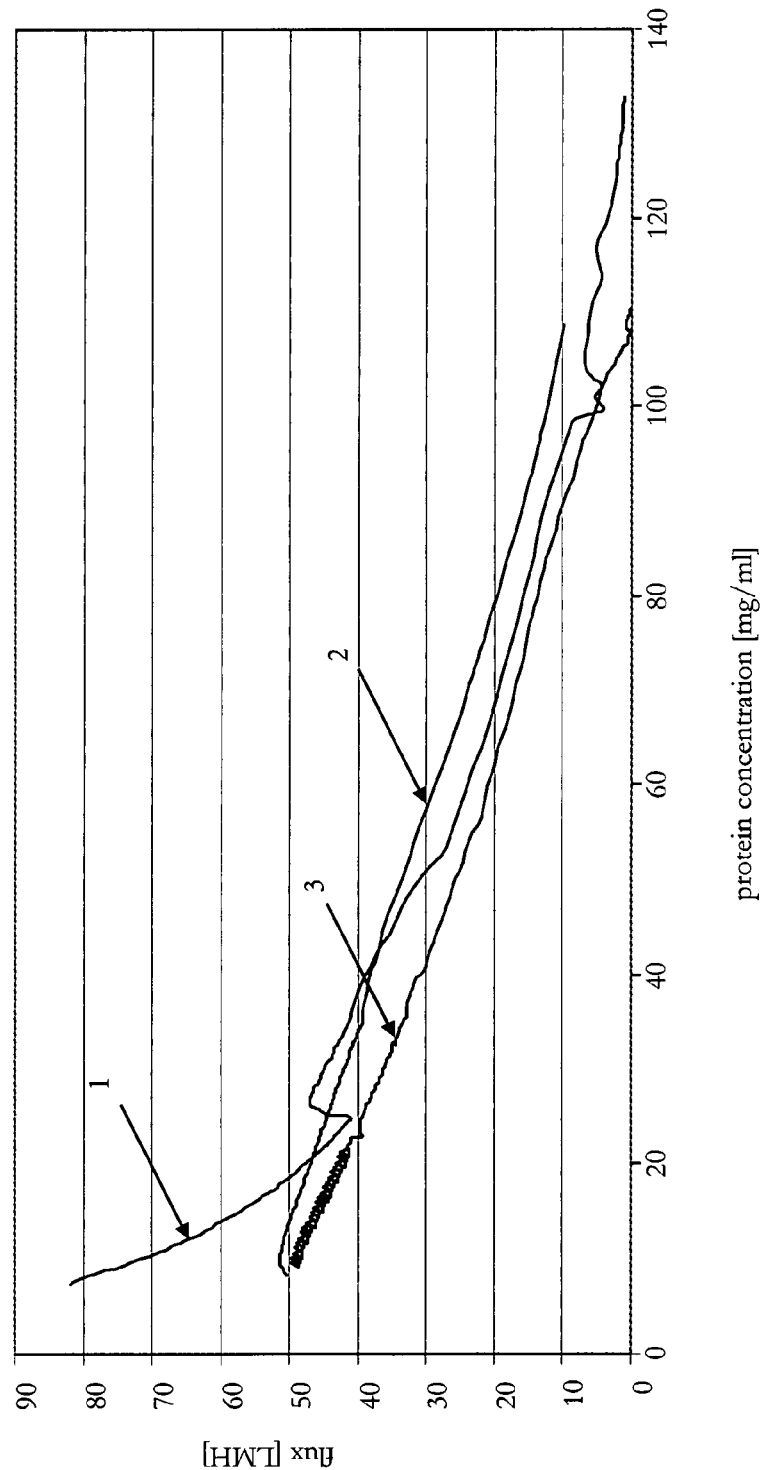
FIG. 4 Flux versus protein concentration of an anti-IL-IR antibody solution. 1: constant method CF=90 ml/min., 2: $\tau_w=541$, 3: variable method according to the invention.
Figure 5:
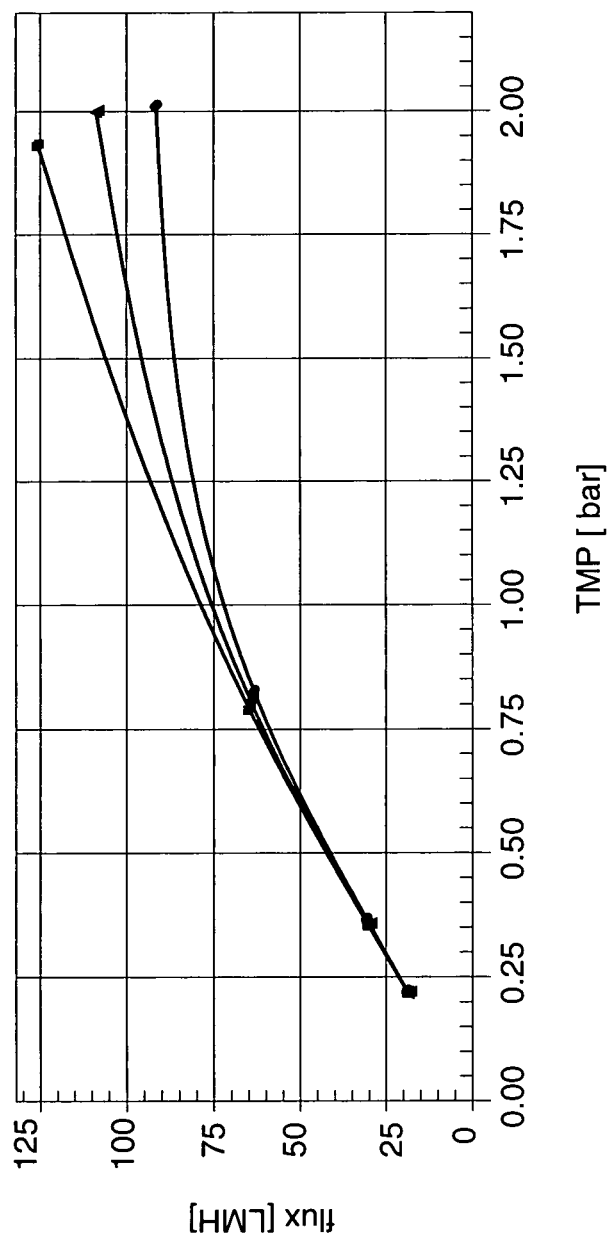
FIG. 5 Transmembrane flux versus transmembrane pressure of an anti-IL-IR antibody solution at a protein concentration of 5.3 mg/ml for cross-flows of 50 ml/min. (filled circles), 80 ml/min. (filled triangles), and 130 ml/min. (filled squares).
Figure 6:
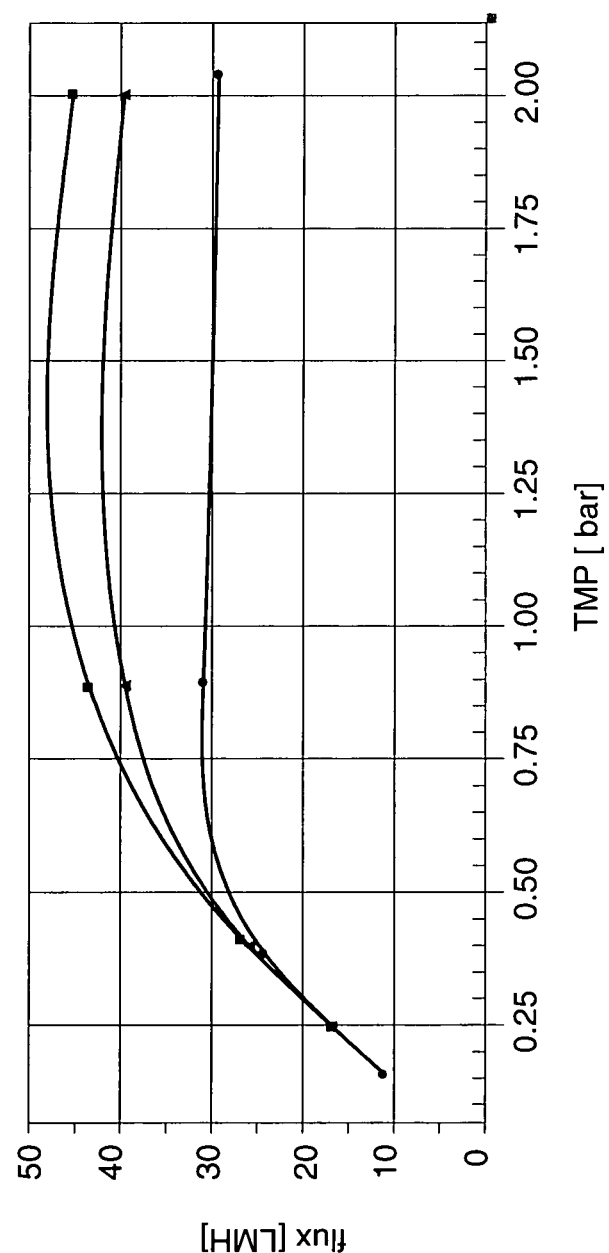
FIG. 6 Transmembrane flux versus transmembrane pressure of an anti-IL-IR antibody solution at a protein concentration of 45 mg/ml for cross-flows of 80 ml/min. (filled circles), 130 ml/min. (filled triangles), and 150 ml/min. (filled squares).
Figure 7:
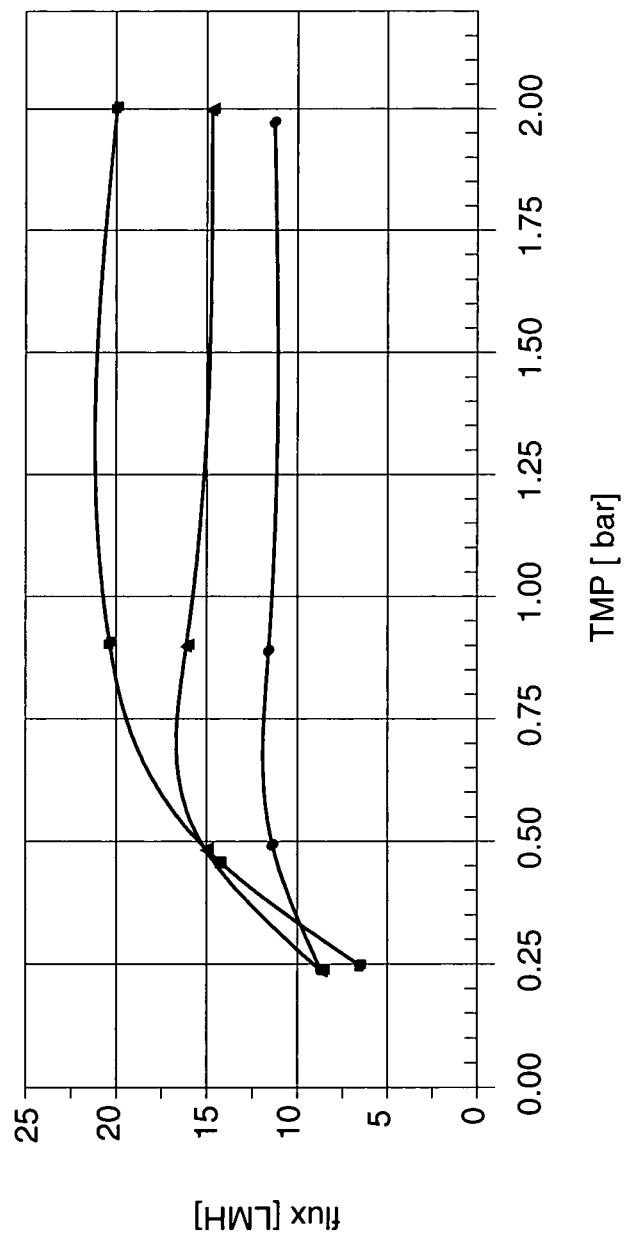
FIG. 7 Transmembrane flux versus transmembrane pressure of an anti-IL-IR antibody solution at a protein concentration of 90 mg/ml for cross-flows of 50 ml/min. (filled circles), 80 ml/min. (filled triangles), and 130 ml/min. (filled squares).
Figure 8:
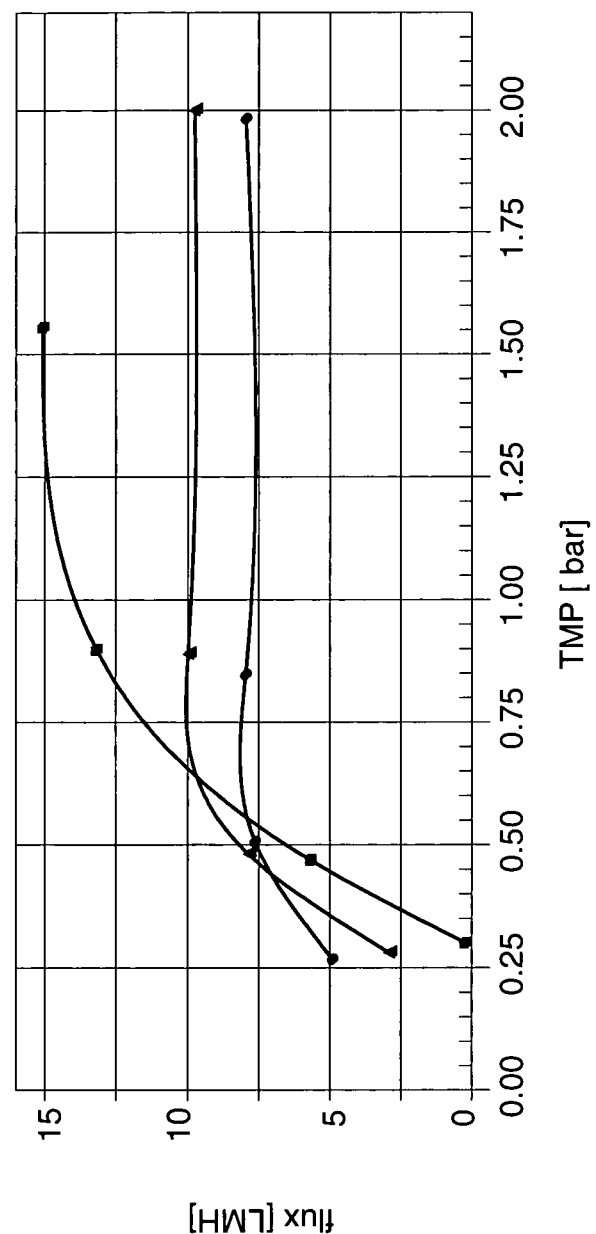
FIG. 8 Transmembrane flux versus transmembrane pressure of an anti-IL-IR antibody solution at a protein concentration of 180 mg/ml for cross-flows of 50 ml/min. (filled circles), 80 ml/min. (filled triangles), and 130 ml/min. (filled squares).

Analytical Methods a) Turbidity Measurement.

The photometric absorbance was determined at 350 nm and 550 nm, where no intrinsic chromophores in the antibody solution absorb (UV-VIS spectrophotometer Evolution 500, Thermo Fisher Scientific, Waltham, USA). The samples were measured undiluted. As a reference medium the appropriate buffer solution was used. Every measurement was conducted three times.

b) Size-Exclusion-HPLC.

The chromatography was conducted with a Tosoh Haas TSK 3000 SWXL column on an ASI-100 HPLC system (Dionex, Idstein, Germany). The elution peaks were monitored at 280 nm by a UV diode array detector (Dionex). After dissolution of the concentrated samples to 1 mg/ml the column was washed with a buffer consisting of 200 mM potassium dihydrogen phosphate and 250 mM potassium chloride pH 7.0 until a stable baseline was achieved. The analyzing runs were performed under isocratic conditions using a flow rate of 0.5 ml/min. over 30 minutes at room temperature. The chromatograms were integrated manually with Chromeleon (Dionex, Idstein, Germany). Aggregation in % was determined by comparing the area under the curve (AUC) of high molecular weight forms with the AUC of the monomer peak.

c) Light Obscuration.

To monitor the particle burden in a range of 1-200 μm a SVSS-C particle analyzer was used (PAMAS Partikelmess- and Analysesysteme, Rutesheim, Germany). The system was calibrated according to the requirements of US Pharmacopeia Vol. 24, <788>, with near-monosize polystyrene spheres. Three measurements of a volume of 0.5 ml with a pre-flushing volume of 0.5 ml were performed. Results were calculated as mean value and referred to a sample volume of 1.0 ml. The number of particles counted was within the sensor's concentration limit.

d) Dynamic Light Scattering (DLS).

DLS is a non-invasive technique for measuring particle size, typically in the sub-micron size range. In the current invention the Zetasizer Nano S apparatus (Malvern Instruments, Worcestershire, UK) with a temperature controlled quartz cuvette (25° C.) was used for monitoring a size range between 1 nm and 6 μm. The intensity of the back scattered laser light was detected at an angle of 173°. The intensity fluctuates at a rate that is dependent upon the particle diffusion speed, which in turn is governed by particle size. Particle size data can therefore be generated from an analysis of the fluctuation in scattered light intensity (Dahneke, B. E. (ed), Measurement of Suspended Particles by Quasielectric Light Scattering, Wiley Inc. (1983); Pecora, R., Dynamic Light Scattering: Application of Photon Correlation Spectroscopy, Plenum Press (1985)). The size distribution by intensity was calculated using the multiple narrow mode of the DTS software (Malvern). Experiments were conducted with undiluted samples.

e) Fourier-Transformed Infrared Spectroscopy.

The FT-IR spectra of the undiluted protein solutions were recorded by using a Tensor 27 spectrometer (Bruker Optik, Ettlingen, Germany) with a flow-through transmission cell (AquaSpec) connected to a thermostat. For each spectrum a 120-scan interferogram was collected at a single-beam mode with a 4 cm$^{-1}$ resolution. As reference media the appropriate permeate was used. The collected interferogram of the protein and the buffer system were Fourier transformed. Further, the spectrum of the protein was corrected for the spectrum of the corresponding buffer system.

EXAMPLE 2

Determination of TMP and CF Conditions

A conditioned and filtered citrate-buffered aqueous solution (pH 5.5) of an anti-IL-IR antibody was concentrated twenty fold up to 100 mg/ml by use of an automated TFF system ÄKTAcrossflow™ (GE Healthcare, Amersham Bioscience AB, Uppsala, Sweden) by employing a scaleable flat sheet cassette (Sartorius, Göttingen, Germany) with a Hydrosart™ membrane of regenerated cellulose, with a nominal molecular weight cut-off of 30 kDa and a membrane area of 0.02 m$^2$. Different concentration programs generated with the UNICORN software controlling ÄKTAcrossflow™ were performed. Total membrane loading was about 400 g/m$^2$.

Flux and pressure profiles at four preset transmembrane pressures are determined at different immunoglobulin concentrations in the immunoglobulin solution to be concentrated with respect to different cross-flows. The TMP was set to 0.3 bar, 0.5 bar, 0.9 bar, or 2.0 bar. The cross-flows for each TMP and protein concentration were 50 ml/min, 80 ml/min, 130 ml/min. (not at 45 mg/ml protein concentration), and 150 ml/min. (only at 45 mg/ml protein concentration). The different protein concentrations were 5.3 mg/ml, 45 mg/ml, 90 mg/ml, and 180 mg/ml. The results are shown in FIGS. 5 to 8.

Figure 9:
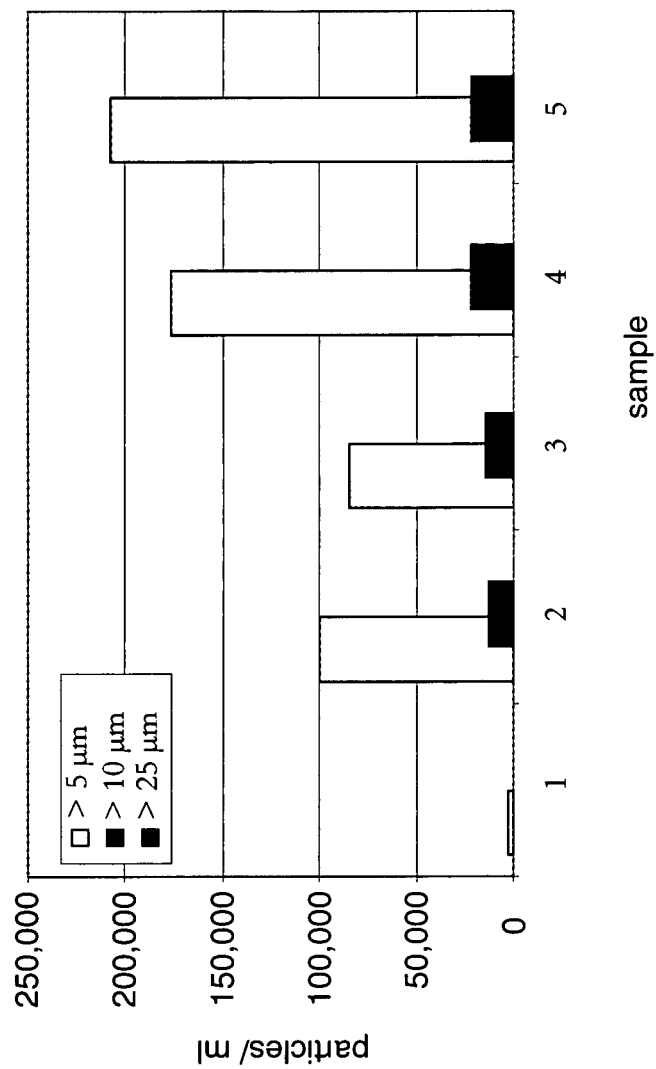
FIG. 9 Particle analysis of the concentrate of an anti-IL-IR antibody solution in citrate buffer obtained by different methods. 1: before concentration, 2: variable method according to the invention, 3: constant method CF 90 ml/min., 4: constant method $\Delta p=1.8$ bar, 5: constant method $\Delta p=3.0$ bar.
Figure 10:
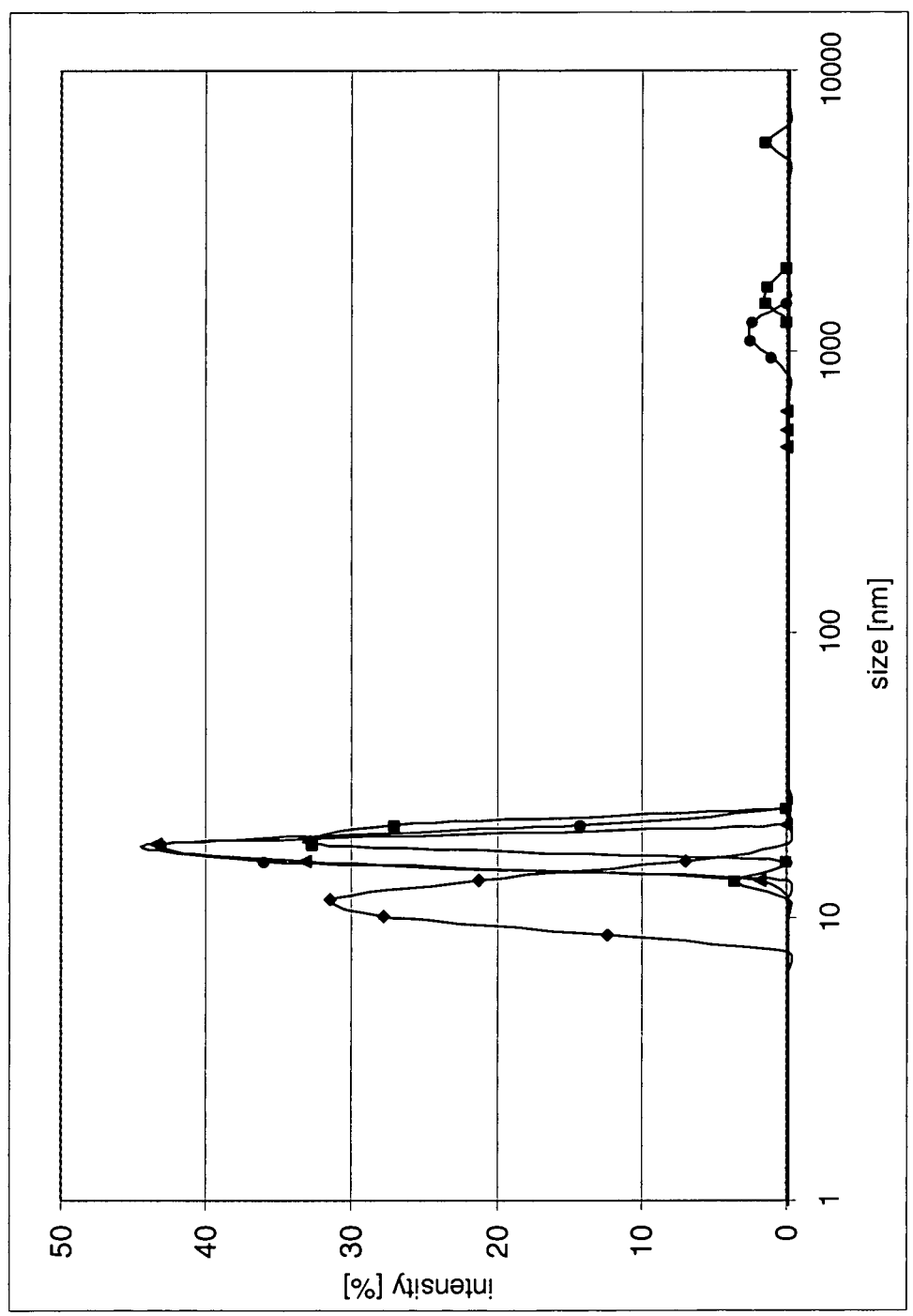
FIG. 10 Dynamic light scattering analysis of the concentrate of an anti-IL-IR antibody solution in citrate buffer obtained by different methods. Filled rhombus: before concentration, filled square: variable method according to the invention, filled triangle: constant method CF 90 ml/min., filled circles: constant method $\Delta P=1.8$ bar.
Figure 11:
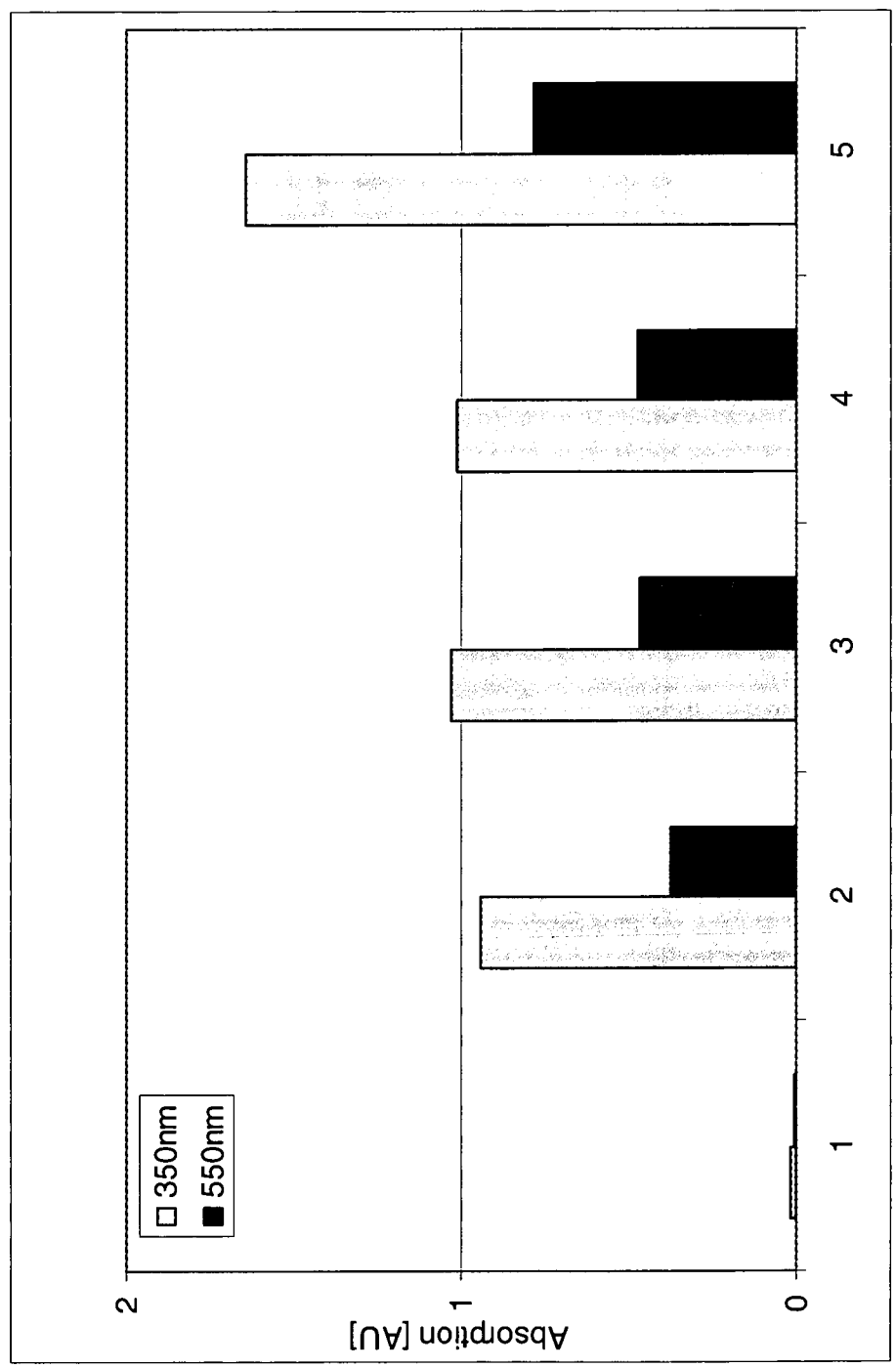
FIG. 11 Turbidity measurement of concentrate of an anti-IL-IR antibody solution in citrate buffer obtained by different methods. 1: before concentration, 2: variable method according to the invention, 3: constant method CF=90 ml/min., 4: constant method $\Delta p=1.8$ bar, 5: constant method $\Delta p=3.0$ bar.

It has been found during the concentration processes that a high feed flux and a high feed pressure result in a good transmembrane flux. But during the concentration process, especially at the end, a polarization layer is established resulting in a membrane overpressure and also a reduced (permeate) flux. It was also found that an increased feed pressure results in a higher flux and therefore a fast concentration process but this acceleration is accompanied by an increased aggregate formation (FIGS. 9 to 11).

Taking into account the above the ranges and conditions for an improved method for immunoglobulin concentration were found to be:
a transmembrane pressure of from 1.4 bar to 1.6 bar and a cross-flow of from 75 ml/min. to 90 ml/min. in a concentration range up to 30 mg immunoglobulin per ml of solution to be concentrated,
a transmembrane pressure of from 0.8 bar to 0.9 bar and a cross-flow of from 140 ml/min. to 160 ml/min. in a concentration range of from 15 mg/ml up to 55 mg/ml, and
a transmembrane pressure of from 0.8 bar to 0.9 bar and a cross-flow of from 120 ml/min. to 140 ml/min. in a concentration range of more than 45 mg/ml.

These parameters result in a method with a reduced aggregate formation and a short concentration time.

EXAMPLE 3

Comparison of the Variable Method According to the Invention to Constant Methods The method according to the invention was compared to different constant parameter methods for the production of a concentrated immunoglobulin solution. The target concentration was set to 90 mg/ml. The tangential flow filtration was performed with the devices according to Example 2. The different parameters of the compared methods (methods 1 to 4 are constant methods, method 5 is the variable method according to the invention) were the following:
Method 1: transmembrane pressure=0.6 bar
cross-flow=90 ml/min
Δp=0.7 bar
Method 2: transmembrane pressure=0.6 bar
Δp=1.2 bar
Method 3: transmembrane pressure=0.6 bar
Δp=1.8 bar
Method 4: transmembrane pressure=0.6 bar
Δp=3.0 bar
Method 5: a) transmembrane pressure=1.5 bar, Δp=0.5 bar,
b) transmembrane pressure=0.85 bar, Δp=1.2 bar,
c) transmembrane pressure=0.85 bar.

The different parameters and the time required to achieve a concentration of the immunoglobulin solution to an immunoglobulin concentration of 90 mg/ml are shown in Table 2.

TABLE 2

Comparison of the parameters for different concentrations methods.

| Method | ΔP | TMP | Feed press | Ret press | Feed flow | Ret flow | Particles >1 μm/ml | time |
|---|---|---|---|---|---|---|---|---|
| 1 | 0.7 bar | 0.6 bar | 1.2 bar | 0.5 bar | 100 ml/min | 90 ml/min | 7321820 | 149 min. |
| 2 | 1.2 bar | 0.6 bar | 1.4 bar | 0.2 bar | 170 ml/min | 160 ml/min | 15403850 | 126 min. |
| 3 | 1.8 bar | 0.6 bar | 2.1 bar | 0.3 bar | 230 ml/min | 215 ml/min | 16989540 | 125 min. |
| 4 | 3.0 bar | 0.6 bar | 2.8 bar | 0.2 bar | 300 ml/min | 280 ml/min | 19415180 | 116 min. |
| 5 | 0.5 bar | 1.5 bar | 2.0 bar | 1.5 bar | 100 ml/min | 80 ml/min | 12182240 | 118 min. |
|  | 1.2 bar | 0.85 bar | 1.7 bar | 0.5 bar | 165 ml/min | 150 ml/min |  |  |
|  | — | 0.85 bar | — | 0.5 bar | 135 ml/min | 130 ml/min |  |  |

From the results of the different methods it can be seen that with method 5, i.e. with a variable method, compared to methods 2 to 4 a dramatically reduced aggregate formation can be obtained and thus an immunoglobulin concentrate with improved characteristics. Compared to method 1 a faster concentration process can be achieved.

EXAMPLE 4

Concentration of an Anti-IL-IR Antibody in Different Buffer Systems

Figure 12:
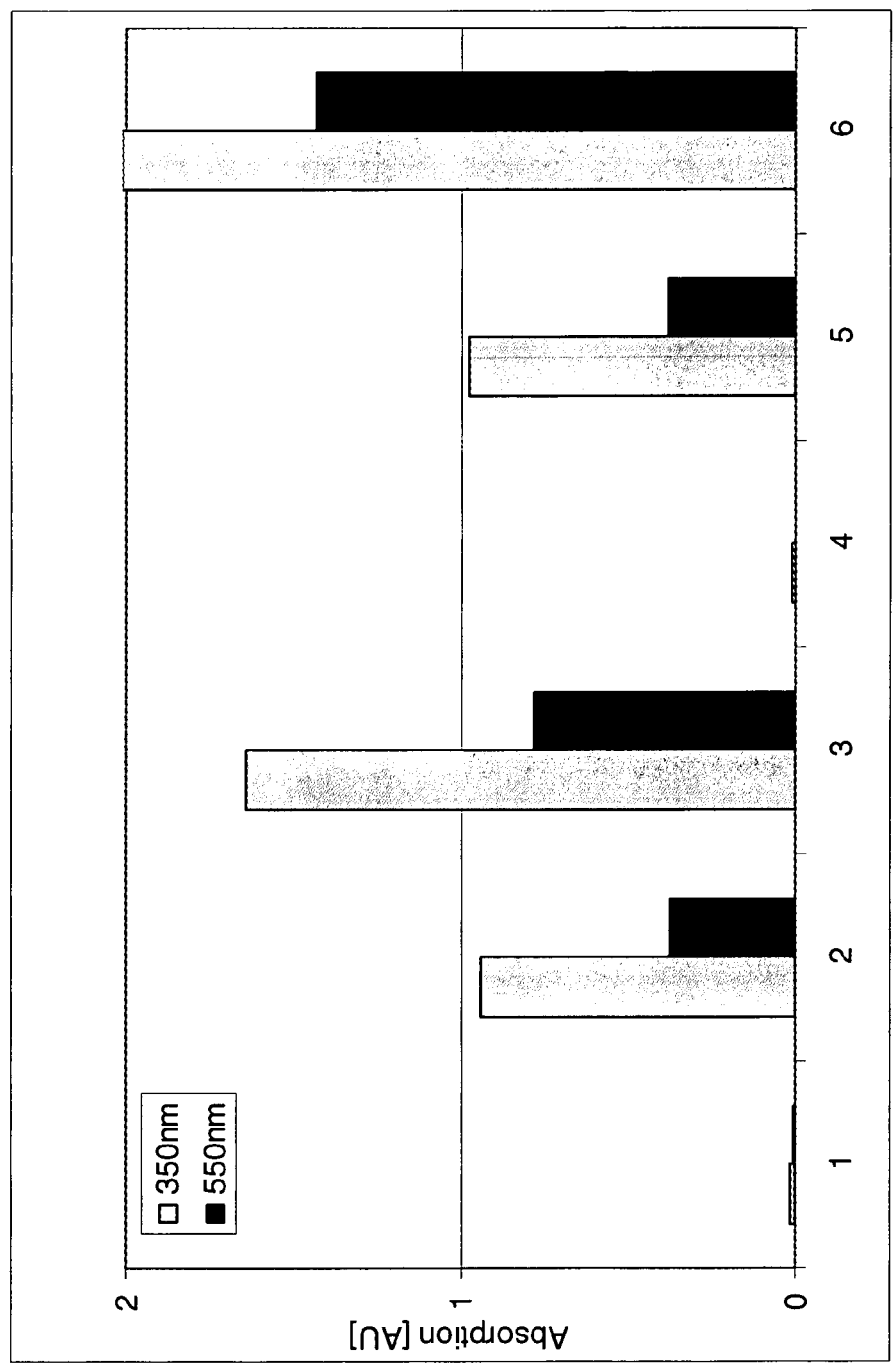
FIG. 12 Turbidity measurement of concentrate of an anti-IL-IR antibody solution obtained with the method according to the invention and a constant method employing different buffers. 1: before concentration in citrate buffer, 2: variable method according to the invention with citrate buffer, 3: constant method $\Delta p=3.0$ bar with citrate buffer, 4: before concentration in histidine buffer, 5: variable method according to the invention with histidine buffer, 6: constant method $\Delta p=3.0$ bar with histidine buffer.
Figure 13:
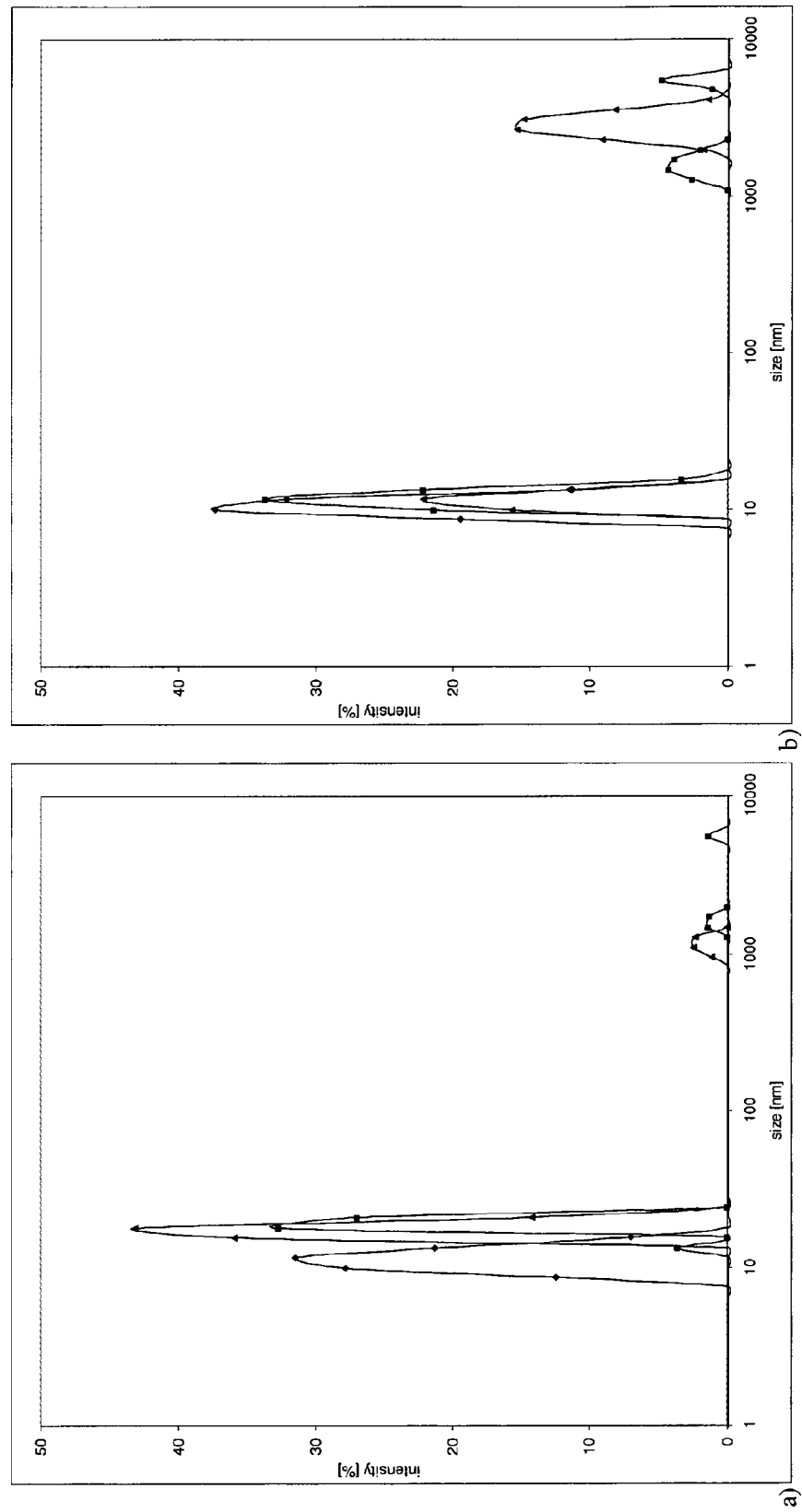
FIG. 13 Dynamic light scattering analysis of the concentrate obtained by different methods and obtained in different buffer: a) anti-IL-IR antibody in citrate buffer (filled rhombus: before concentration, filled square: after concentration with variable method according to the invention, filled triangle: constant method $\Delta p=1.8$ bar), b) anti-IL-IR antibody in histidine buffer (filled rhombus: before concentration, filled square: after concentration with variable method according to the invention, filled triangle: constant method $\Delta p=3.0$ bar).

A comparative concentration of an aqueous anti-IL-IR antibody solution buffer with citrate buffer or histidine buffer was performed with the device of Example 2 and the method according to the invention (method S of Example 3). The results are shown in FIGS. 12 and 13. From FIG. 12 and FIG. 13, respectively, can be seen that the employed buffer has no effect on the concentration process according to the invention.

EXAMPLE 5

Concentration of an Anti-P-Selectin Antibody

Figure 14:
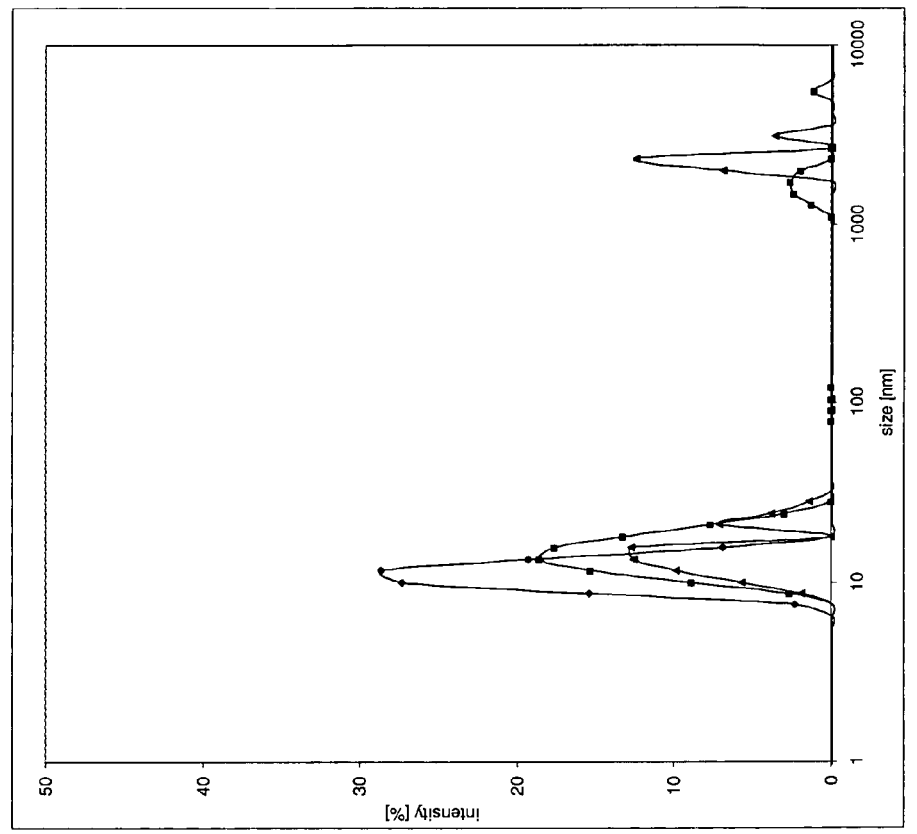
FIG. 14 Turbidity measurement (a) and dynamic light scattering (b) results of the concentration of an anti-P-selectin antibody in histidine buffer. 1: before concentration (filled rhombus), 2: variable method according to the invention (filled square), 3: constant method $\Delta p=3.0$ bar (filled triangle).
Figure 14:
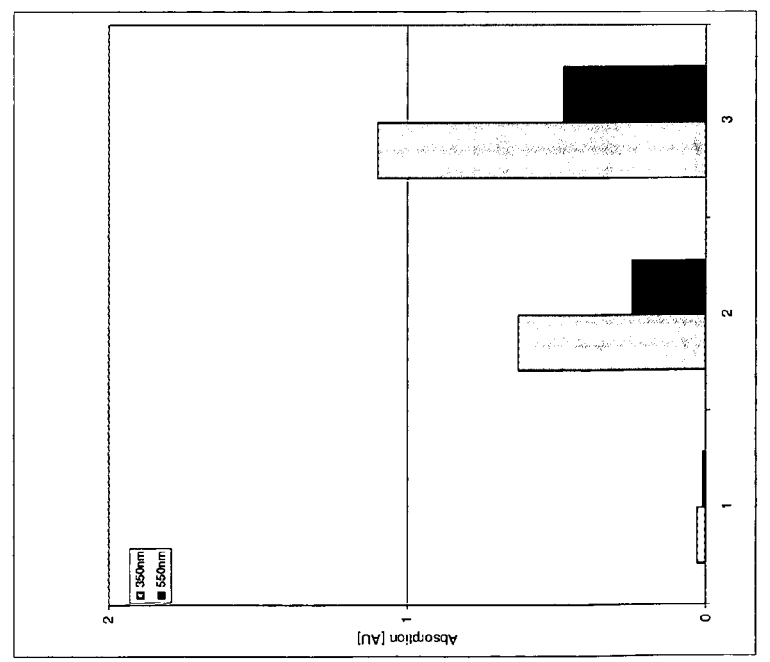

The concentration of an anti-P-selectin antibody was performed according to the method of Example 2 and the results are shown in FIG. 14.

EXAMPLE 6

Filtration of Concentrated Solution

The concentrated solution obtained according to the method of Example 2 was filtrated after the tangential flow filtration with a pressure of 0.75 bar through a Durapore (PVDF, Millipore GmbH, Schwalbach, Germany) membrane (4.52 cm$^2$ filter area).

Figure 15:
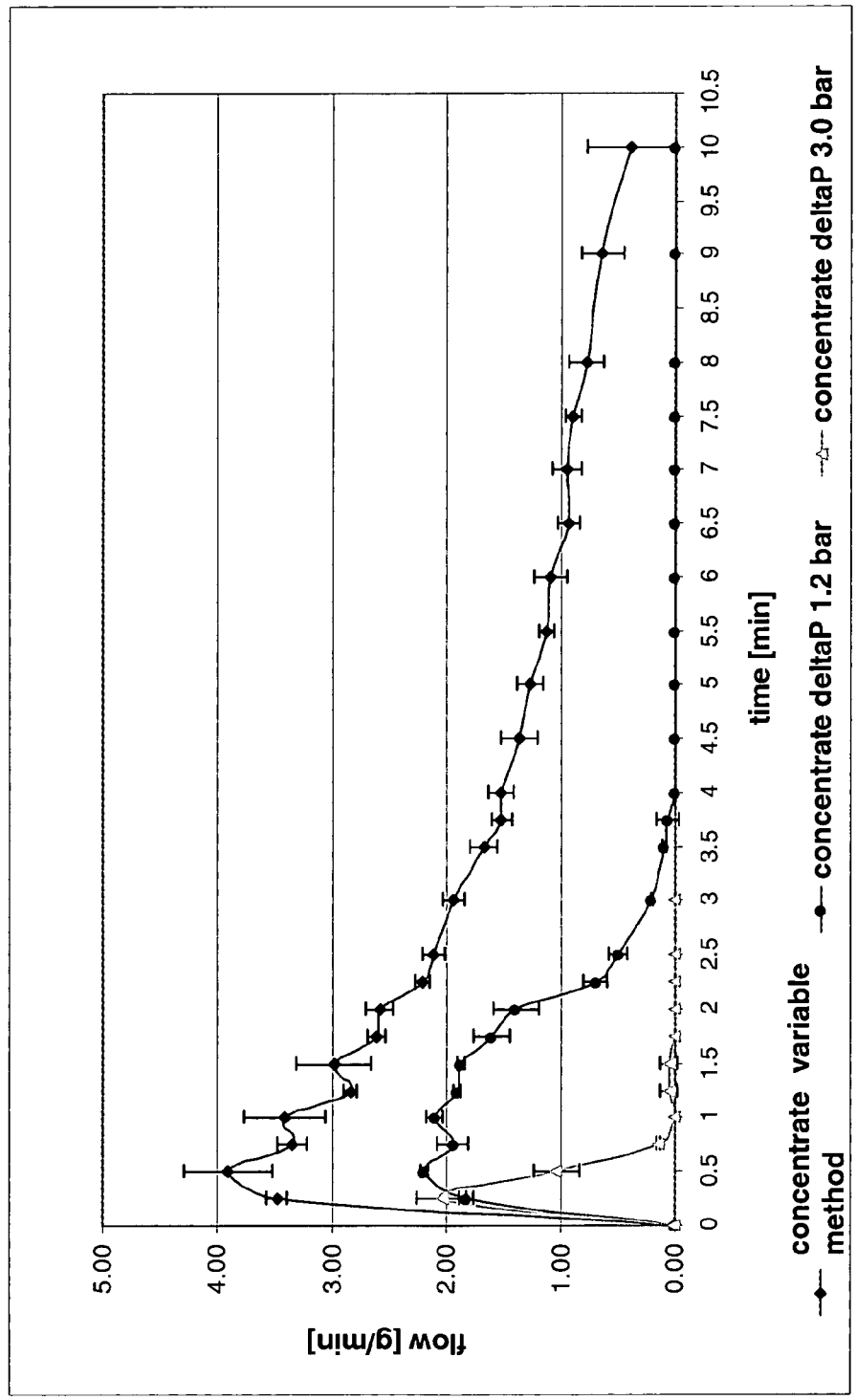
FIG. 15 Effect of concentration mode on filterability of concentrated immunoglobulin solutions.

It has been found that the filterability of highly concentrated immunoglobulin solutions depends on the employed concentration method. It has further been found that the concentrated immunoglobulin solution obtained with the variable method according to the invention show a reduced decline in the filtration flow when compared with other fixed methods (FIG. 15).

The invention claimed is:

1. A method for concentrating an immunoglobulin solution by tangential flow filtration, characterized in that the transmembrane pressure and the cross-flow are variable, and changed during the filtration process according to the concentration of the immunoglobulin to be concentrated, wherein i) a transmembrane pressure of from 1.4 bar to 1.6 bar and a cross-flow of from 75 ml/min. to 90 ml/min. is applied in a concentration range up to 30 mg immunoglobulin per ml of solution to be concentrated, ii) a transmembrane pressure of from 0.8 bar to 0.9 bar and a cross-flow of from 140 ml/min. to 160 ml/min. is applied in a concentration range of from 15 mg/ml up to 55 mg/ml, and iii) a transmembrane pressure of from 0.8 bar to 0.9 bar and a cross-flow of from 120 ml/min. to 140 ml/min is applied in a concentration range of more than 45 mg/ml up to about 130 mg/ml.

2. The method of claim 1, wherein the transmembrane pressure and cross-flow in i) are 1.5 bar and 80 ml/min., in ii) are 0.85 bar and 150 ml/min., and;

in iii) are 0.85 bar and 130 ml/min.

3. The method of claim 1, wherein the concentration range is in i) of 5 to 25 mg/ml, in ii) of from 25 to 50 mg/ml, and in iii) from 50 to 140 mg/ml.

4. A method for producing a heterologous immunoglobulin comprising:

a) providing a recombinant mammalian cell comprising one or more nucleic acids encoding a heterologous immunoglobulin, b) cultivating said cell under conditions suitable for the expression of the heterologous immunoglobulin, c) recovering the heterologous immunoglobulin from the recombinant mammalian cell or the culture medium; and d) concentrating the obtained aqueous, buffered solution comprising the heterologous immunoglobulin using a tangential flow filtration wherein the concentration of the heterologous immunoglobulin determines the transmembrane pressure and cross flow in said filtration and wherein the variable transmembrane pressure and cross-flow of step d) are selected from the group consisting of i) a transmembrane pressure of from 1.4 bar to 1.6 bar and a cross-flow of from 75 ml/min to 90 ml/min. in a concentration range up to 30 mg immunoglobulin per ml of solution to be concentrated, ii) a transmembrane pressure of from 0.8 bar to 0.9 bar and a cross-flow of from 140 ml/min. to 160 ml/min. in a concentration range of from 15 mg/ml up to 55 mg/ml, iii) a transmembrane pressure of from 0.8 bar to 0.9 bar and a cross-flow of from 120 ml/min. to 140 ml/min. in a concentration range of more than 45 mg/ml up to about 130 mg/ml.

5. The method of claim 4, further comprising prior to or after step d), the following:
   e) purifying the aqueous buffered solution containing the heterologous immunoglobulin.

6. The method of claim 5, wherein the heterologous immunoglobulin is a complete immunoglobulin, or an immunoglobulin fragment, or an immunoglobulin conjugate.

7. The method of claim 6, characterized in that the mammalian cell is a CHO cell, a BHK cell, a HEK cell, or a Sp2/0 cell.

8. The method of claim 4, wherein said tangential flow filtration employs a membrane with a cut off value in the range of from 20 to 50 kDa molecular weight.

9. The method of claim 4, wherein said immunoglobulin solution has a pH value of from pH 3.0 to pH 10.0.

10. The method claim 9, wherein said pH value is in the range of from pH 3.0 to pH 7.0.

11. The method of claim 4, characterized in that said method is a variable tangential flow filtration method wherein the actual concentration of the immunoglobulin in the solution to be concentrated determinates the applied transmembrane pressure and cross-flow.

12. The method of claim 4, characterized in that the transmembrane pressure and cross-flow can be changed at any concentration value in the overlapping concentration ranges.

13. The method of claim 4, characterized in that the concentration range is
   in i) of 5 to 25 mg/ml,
   in ii) of from 25 to 50 mg/ml, and
   in iii) of from 50 to 140 mg/ml.

\* \* \* \* \*

UNITED STATES PATENT AND TRADEMARK OFFICE
CERTIFICATE OF CORRECTION

PATENT NO. : 8,633,302 B2  Page 1 of 1
APPLICATION NO. : 12/668661
DATED : January 21, 2014
INVENTOR(S) : Hepbildikler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 738 days.

Signed and Sealed this
Twenty-second Day of September, 2015

Michelle K. Lee
*Director of the United States Patent and Trademark Office*